United States Patent [19]

Sshiwata et al.

[11] Patent Number: 5,443,973
[45] Date of Patent: Aug. 22, 1995

[54] METHOD OF PRODUCING α-HYDROXYISOBUTYRAMIDE FROM ACETONE CYANOHYDRIN BY NITRIL HYDRATASE

[75] Inventors: Kenichi Sshiwata; Masao Shimada, both of Kanagawa; Akira Hatamori, Chiba, all of Japan

[73] Assignee: Mitsui Toatsu Chemicals, Inc., Tokyo, Japan

[21] Appl. No.: 929,574

[22] Filed: Aug. 19, 1992

[30] Foreign Application Priority Data

Aug. 16, 1991 [JP] Japan ............................. 3-206032
Nov. 21, 1991 [JP] Japan ............................. 3-305995

[51] Int. Cl.[6] .................... C12P 13/02; C12N 9/78
[52] U.S. Cl. ........................... 435/129; 435/227
[58] Field of Search .......................... 435/129, 227

[56] References Cited

U.S. PATENT DOCUMENTS

| | | | |
|---|---|---|---|
| 4,001,081 | 1/1977 | Commeyras | 435/129 |
| 4,464,539 | 8/1984 | Hashimoto et al. | 560/212 |
| 4,637,982 | 1/1987 | Yamada | 435/129 |
| 5,179,014 | 1/1993 | Watanabe | 435/129 |
| 5,200,331 | 4/1993 | Kawakami | 435/129 |

FOREIGN PATENT DOCUMENTS

| | | | |
|---|---|---|---|
| 0187681 | 7/1986 | European Pat. Off. | 435/129 |
| 307926 | 3/1988 | European Pat. Off. | |
| 0407811 | 1/1991 | European Pat. Off. | |
| 62-267255 | 11/1987 | Japan | |
| 5-219972 | 8/1993 | Japan | |
| 2086892 | 5/1982 | United Kingdom | |

OTHER PUBLICATIONS

Klibanov, A., "Enzymes that work in Organic Solvents", *Chemtech*, pp. 354–359, 1986.
Klibanov, A., "Enzymelic Catalysis in Anhydrous Organic Solvents", *TIBS* Apr. 1989.
Zaks, A. et al, "Enzyme–catalyzed Processes in Organic Solvent", vol. 82 pp. 3192–3196, 1985.
"Substrates and Inhibitors of the Nitrile Hydratase and Amidase of Corynebacterium nitrilophilus", T. Amarant et al, Biotech. & Applied Bichem. vol. 11, pp. 49–59 (1989).

*Primary Examiner*—Irene Marx
*Attorney, Agent, or Firm*—Burns, Doane, Swecker & Mathis

[57] ABSTRACT

A culture liquid of microorganisms having an ability of producing α-hydroxyisobutylamide from acetone cyanhydrin or the cultivated cells of the microorganisms or the processed cells of them is/are reacted to acetone cyanhydrin in an aqueous medium to produce α-hydroxyisobutylamide. The amide is reacted with water and/or an aliphatic alcohol in the presence of a solid acid catalyst at a temperature of 150° C. or higher in a gaseous phase or a gaseous-liquid mixed phase to produce an α,β-unsaturated carboxylate or an aliphatic alcohol or an α,β-unsaturated carboxylic acid.

18 Claims, No Drawings

METHOD OF PRODUCING α-HYDROXYISOBUTYRAMIDE FROM ACETONE CYANOHYDRIN BY NITRIL HYDRATASE

DETAILED EXPLANATION OF THE INVENTION

Field of the Invention

The present invention relates to a method of producing α-hydroxyisobutyramide from acetone cyanohydrin and to a method of producing α,β-unsaturated carboxylates of aliphatic alcohols or α,β-unsaturated carboxylic acids from the amide.

α-hydroxyisobutyramide is an industrially useful substance as an intermediate material for producing methyl methacrylate; and methyl methacrylate is as a raw material of producing acrylic resins.

Prior Art

Heretofore, as a typical method of producing α-hydroxyisobutyramide, a method of producing it by hydration of acetone cyanohydrin with a catalyst of manganese oxide is known (for example, DE 2527120).

On the other hand, known is a method of producing various amides from the corresponding nitriles by the action of nitrile hydrarase which is an enzyme to be produced by microorganisms. For instance, production of acrylamide, acetamide, methacrylamide, crotonamide, 3-hydroxypropionamide, nicotinamide and benzamide may be enzymatically produced from the corresponding nitriles (for example, EP 307926). However, neither microorganisms nor enzymes are known at all, which produce α-hydroxyisobutyramide from acetone cyanohydrin. Further, with respect to nitrile hydratase derived from *Corynebacterium nitrilophilus*, it is reported that acetone cyanohydrin could not be a substrate for it but rather is a substance of strongly inhibiting with the activity of nitrile hydratase (*Biotechnology and Applied Biochemistry*, Vol. 11, pp. 49–59 (1989)).

PROBLEMS TO BE SOLVED BY THE INVENTION

The object of the present invention is to efficiently produce α-hydroxyisobutyramide from acetone cyanohydrin by the use of microorganisms having an ability of producing α-hydroxyisobutyramide from acetone cyanohydrin and to produce α,β-unsaturated carboxylates of aliphatic alcohols or α,β-unsaturated carboxylic acids by the use of the amide.

MEANS FOR SOLVING THE PROBLEMS

The present inventors repeatedly studied to find a novel method of producing α-hydroxyisobutyramide and, as a result, have found microorganisms having an ability of producing α-hydroxyisobutyramide from acetone cyanohydrin and also have found that α-hydroxyisobutyramide may efficiently be produced by reacting a culture liquid of such microorganisms, the cultivated cells of them or the processed cells of them, as an enzyme source, to acetone cyanohydrin in an aqueous medium and that methyl methacrylate is produced from the amide. On the basis of the findings, they have completed the present invention.

Specifically, the present invention provides a method of producing α-hydroxyisobutyramide by reacting a culture liquid of microorganisms having an ability of producing α-hydroxyisobutyramide from acetone cyanohydrin or the cultivated cells of the microorganisms or the processed cells of them, to acetone cyanohydrin in an aqueous medium, and also provides a method of producing α,β-unsaturated carboxylates of aliphatic alcohols or α,β-unsaturated carboxylic acids by reacting the amide and water and/or an aliphatic alcohol in the presence of a solid acid catalyst at a temperature of 150° C. or higher in a gaseous phase or in a gaseous-liquid mixed phase.

The microorganisms to be used in the present invention are not specifically limited, provided that they have an ability of producing α-hydroxyisobutyramide from acetone cyanohydrin. They may be ones separated from the natural field or may also be ones as created by mutation, genetic operation or the like means.

As examples of such microorganisms, the following are mentioned.

*Rhodococcus erythropolis* ATCC 4277, ATCC 11048, MT 20082 (FERM BP-3933)
*Rhodococcus* sp. MT 20118 (FERM BP-3934)
*Arthrobacter paraffineus* ATCC 21003
*Achromobacter xerosis* IFO 12668
*Acinetobacter calcoaceticus* IFO 12552
*Pseudomonas fluorescens* IFO 3925

*Achromobacter xerosis* IFO 12668, *Acinetobacter calcoaceticus* IFO 12552, and *Pseudomonas fluorescens* IFO 3925 are available from IFO: INSTITUTE FOR FERMENTATION, OSAKA of 17–85, Juso-honmachi 2-chrome, Yodogawa-ku, Osaka 532, Japan. *Rhodococcus erythropolis* ATCC 4277, *Rhodococcus erythropolis* ATCC 11048, and *Arthrobacter paraffineus* ATCC 21003 are available from ATCC: American Type Culture Collection of 12301 Parklawn Drive, Rockville, Md. 20852, USA.

The medium for cultivating the microorganisms to be used in the present invention is not specifically defined, provided that it attains the object. Any of synthetic media and natural media may be used, suitably containing carbon sources, nitrogen sources, inorganic salts and microorganic nutrients which may be assimilated by the microorganisms to be cultivated. In cultivation of the microorganisms, amides such as crotonamide may be added to the medium whereby cells of the microorganisms having a high ability of producing α-hydroxyisobutyramide from acetone cyanohydrin may often be obtained. In the case, the preferred amount of the amides to be added is approximately from 0.1 to 5 %.

The cultivation conditions vary, depending upon the microorganisms to be cultivated or the medium to be used. Desirably, the cultivation temperature is from 20 to 40° C., and the pH of the medium is from 4 to 9.

In the present invention, the culture liquid thus obtained, the cells of the cultivated microorganisms as collected by centrifugation or filtration, or the processed cells of them is/are used as an enzyme source. The processed cells include, for example, those obtained by processing the collected cells by mechanical destruction, ultrasonic treatment, freezing and thawing treatment, drying treatment, solvent treatment, pressure or reduced pressure treatment, osmotic pressure treatment, autolysis, surfactant treatment or enzyme treatment, as well as immobilized products of the enzyme fractions, the cells and the cell extracts to be obtained from them. For immobilization of the enzyme or the cells any conventional method can be used (*Method in Enzymology*, Vol. 44 (1976); ibid., Vols. 135 and 136 (1987); ibid., Vol. 137 (1988)). For instance, usable are (1) a carrier binding method in which enzyme or cells are bonded to a water-insoluble carrier by physical adsorption, ion bonding or covalent bonding; (2) a crosslinking method in which enzyme or cells are cross-linked with a chemical reagent having two or more functional groups; and (3) a microcapsule type inclusion method in which enzyme or cells are coated with a lattice type or semipermeable high polymer film capable of capturing them in the fine lattices of a high polymer gel. They may be suitably selected and used in the present invention. The amount of the cells to be added is not specifically defined but is generally suitably from 1 to 100 g (as dry cells)/liter (this means the weight of dry cells per the unit of the reaction solution and is hereinafter simply represented by g/liter unless otherwise specifically defined).

The reaction is effected by bringing the enzyme source into contact with acetone cyanohydrin at a temperature of from 0° to 50° C. and at a pH of from 5 to 10 in an aqueous medium under static or gently stirring condition. By adding acetone to the aqueous medium, the yield of α-hydroxyisobutyramide to be produced may be elevated. The amount of acetone to be added is preferably 4M or less. If it is higher than the defined range, the enzyme activity in the reaction system would be inhibited thereby. Since acetone cyanohydrin is in a dissociation equilibrium of acetone and prussic acid in the reaction medium, a mixture comprising acetone and prussic acid (or salts of prussic acid) may be used as a substrate in place of acetone cyanohydrin. The reaction time varies, depending upon the reaction conditions of the enzyme titer and the substrate concentration, and is generally approximately from 1 to 50 hours. The concentration of the substrate acetone cyanohydrin is not specifically defined but is generally approximately from 0.1 to 30 % by weight. In carrying out the present invention, acetone cyanohydrin can be added to the reaction solution either continuously or intermittently.

After carrying out the reaction in this way, α-hydroxyisobutyramide is formed in the reaction solution. For collecting the thus formed α-hydroxyisobutyramide from the reaction solution, any known method such as concentration, crystallization or the like can be employed.

The α-hydroxyisobutyramide thus obtained in the manner mentioned above may be used for producing α,β-unsaturated carboxylates of aliphatic alcohols or α,β-unsaturated carboxylic acids, by reacting it with water and an aliphatic alcohol in the presence of a solid acid catalyst at a temperature of 150° C. or higher in a gaseous phase or a gaseous-liquid mixed phase. For the method, for example, suitably usable is a method as described in Japanese Patent Publication No. 63-10940 (U.S. Pat. No. 4,464,539).

The solid acid catalyst to be used in production of such α,β-unsaturated carboxylates of aliphatic alcohols or α,β-unsaturated carboxylic acids is a catalyst containing at least one of phosphates, sulfates, halides, oxides and sulfides of at least one selected from metal elements and non-metal elements of the Groups I, IIa, IVa and Va of the Periodic Table. As particular examples, it also includes active charcoal, cation exchange resins, and α-boron and nickel metals.

As aliphatic alcohols, various aliphatic alcohols and substituted aliphatic alcohols are referred to, including, for example, methyl alcohol, ethyl alcohol, n-propyl alcohol, i-propyl alcohol, i-butyl alcohol, ethylene glycol, ethylene glycol monomethyl ether, propylene glycol monomethyl ether, etc.

As reaction of producing α,β-unsaturated carboxylates of aliphatic alcohols or α,β-unsaturated carboxylic acids from α-hydroxyisobutyramide, preferred is a method of bringing the reactant substances into contact with a solid acid catalyst, which is effected in a gaseous phase or a gaseous-liquid mixed phase. The amount of water to be used in the reaction is not specifically defined but, in general, it may be within the range of from 0 to 200 mols, preferably from 1 to 50 mols, to mol of α-hydroxyisobutyramide. The amount of alcohol to be used is not also specifically defined. Where α,β-unsaturated carboxylic acids only are obtained, use of alcohol is unnecessary. In general, the amount of alcohol to be used may be within the range of from 0 to 200 mols, preferably from 1 to 50 mols, to mol of α-hydroxyisobutyramide. The reaction temperature may be from 150° C. to 500° C., preferably from 200° C. to 450° C. The contact time of the reactants varies, depending upon the reaction conditions of the catalyst used and the reaction temperature, and may be generally within the range of from 0.5 to 360 seconds.

EXAMPLES

The present invention will be explained concretely by way of the following examples hereunder. Quantitative determination of α-hydroxyisobutyramide was effected by liquid chromatography equipped with a strong acid cation exchange resin-filled column and an UV absorption detector.

EXAMPLE 1

*Rhodococcus erythropolis* MT 20082 (FERM BP-3933) was inoculated in 100 ml of a liquid medium (pH 7.0) containing 1% of meat extract, 1% of peptone, 0.5 % of NaCl and 0.2 % of crotonamide, and cultivated therein by shaking culture at 28° C. for 24 hours. The cells were separated from the culture liquid by centrifugation, washed and then freeze-dried. Reaction was effected in an aqueous solution (having pH of 8.5 as adjusted with NaOH) containing 40 g/liter of acetone cyanohydrin and 20 g/liter of the freeze-dried cells, at 8° C. for 10 hours with gently stirring. After the reaction, a part of the reaction solution was diluted and analyzed by liquid chromatography, whereupon 30 g/liter of α-hydroxyisobutyramide was found to have accumulated therein. The molar yield was 62 %.

EXAMPLE 2

Reaction was effected in the same manner as in Example 1, except that the cell strain as shown in Table 1 was used. As a result, formation of α-hydroxyisobutyramide of the amount as indicated in Table 1 in each reaction solution was identified.

TABLE 1

| Cell Strain Used | α-hydroxyisobutyramide (g/liter) |
|---|---|
| *Rhodococcus erythropolis* ATCC 4277 | 4 |
| *Rhodococcus erythropolis* ATCC 11048 | 11 |

EXAMPLE 3

*Arthrobacter paraffineus* ATCC 21003 was inoculated in 100 ml of a liquid medium (pH 7.0) containing 1% of meat extract, 1% of peptone, 0.5 % of NaCl and 0.2 % of crotonamide, and cultivated therein by shaking culture at 28° C. for 24 hours. The cells were separated from the culture liquid by centrifugation, washed and then freeze-dried. Reaction was effected in an aqueous solution (having pH of 8.5 as adjusted with NaOH) containing 40 g/liter of acetone cyanohydrin and 20 g/liter of the freeze-dried cells, at 8° C. for 10 hours with gently stirring. After the reaction, a part of the reaction solution was diluted and analyzed by liquid chromatography, whereupon 27 g/liter of α-hydroxyisobutyramide was found to have accumulated therein. The molar yield was 57 %.

EXAMPLE 4

Reaction was effected in the same manner as in Example 3, except that the cell strain as shown in Table 2 was used. As a result, formation of α-hydroxyisobutyramide of the amount as indicated in Table 2 in each reaction solution was identified.

TABLE 2

| Cell Strain Used | α-hydroxyisobutyramide (g/liter) |
|---|---|
| Achromobacter xerosis IFO 12668 | 8 |
| Acinetobacter calcoaceticus IFO 12552 | 4 |
| Pseudomonas fluorescens IFO 3925 | 2 |

EXAMPLE 5

*Rhodococcus sp.* MT 20118 (FERM BP- 3934) was inoculated in 100 ml of a liquid medium (pH 7.0 ) containing 1% of meat extract, 1% of peptone, 0.5 % of NaCl and 0.2 % of crotonamide, and cultivated therein by shaking culture at 30° C. for 36 hours. The cells were separated from the culture liquid by centrifugation, washed and then frozen. Reaction was effected in an aqueous solution (having pH of 8.5 as adjusted with NaOH) containing 20 g/liter of acetone cyanohydrin and 2 g/liter of the frozen cells, at 8° C. for 8 hours with gently stirring. After the reaction, a part of the reaction solution was diluted and analyzed by liquid chromatography, whereupon 16 g/liter of hydroxyisobutyramide was found to have accumulated therein. The molar yield was 66 %.

EXAMPLE 6

Reaction was effected in the same manner as in Example 5, except that 58 g/liter of acetone was added to the reaction solution. After the reaction, formation of 22.5 g/liter of α-hydroxyisobutyramide in the reaction solution was identified. The molar yield was 93%.

EXAMPLE 7

Each of the cell strains as indicated in Table 3 below was inoculated in 100 ml of a liquid medium (pH 7.0) containing 1% of meat extract, 1% of peptone, 0.5 % of NaCl and 0.2 % of crotonamide, and cultivated therein by shaking culture at 28° C. for 40 hours, The cells were separated from the culture liquid by centrifugation, washed and then frozen. Reaction was effected in an aqueous solution (having pH of 7.5 as adjusted with NaOH) containing 20 g/liter of acetone cyanohydrin, 0 or 58 g/liter of acetone and 50 g/liter of the frozen cells, at 10° C. for 12 hours with gently stirring. As a result, formation of α-hydroxyisobutyramide of the amount as indicated in Table 3 in each reaction solution was identified.

TABLE 3

| Cell Strain Used | α-hydroxyisobutyramide (g/liter) | |
|---|---|---|
| | without acetone | with acetone |
| Achromobacter xerosis IFO 12668 | 9 | 14 |
| Acinetobacter calcoaceticus IFO 12552 | 5.5 | 13 |
| Arthrobacter paraffineus IFO 12552 | 11 | 19 |
| Pseudomonas fluorescens IFO 3925 | 3 | 8 |

EXAMPLE 8

*Rhodococcus sp.* MT 20118 (FERM BP- 3934) was inoculated in 100 ml of a liquid medium (pH 7.0 ) containing 1% of meat extract, 1% of peptone, 0.5 % of NaCl and 0.2 % of crotonamide, and cultivated therein by shaking culture at 25° C. for 56 hours. The cells were separated from the culture liquid by centrifugation, washed and then collected. Reaction was effected in such a way that 80 mg of potassium prussiate was intermittently added, at regular intervals of two hours with a pump, to 100 ml of an aqueous solution containing 58 g/liter of acetone and 150 g/liter of the wet cells (40 g/liter of dry cells) with gently stirring at 5° C. while the pH value of the reaction system was adjusted to be 8.8 with $H_2SO_4$. After 20 hours, a part of the reaction solution was diluted and analyzed by liquid chromatography, whereupon 10 g/liter of α-hydroxyisobutyramide was found to have accumulated therein. The molar yield to potassium prussiate was 78 %.

EXAMPLE 9

*Rhodococcus sp.* MT 20118 (FERM BP- 3934) was inoculated in 6000 ml of a liquid medium (pH 7.0) containing 1% of meat extract, 1% of peptone, 0.5 % of NaCl and 0.2 % of crotonamide, and cultivated therein by shaking culture at 28° C. for 45 hours. The cells were separated from the culture liquid by centrifugation, washed and then freeze-dried. Reaction was effected in such a way that 0.45 g per hour of acetone cyanohydrin was continuously added to 30 ml of an aqueous solution containing 6 g/liter of acetone and 25 g/liter of the freeze-dried cells, with a pump with gently stirring at 6° C. while the pH value of the reaction system was adjusted to be 8.3 with NaOH. After 24 hours, a part of the reaction solution was diluted and analyzed by liquid chromatography, whereupon 303 g/liter of αhydroxyisobutyramide was found to have accumulated therein. The molar yield was 93 %.

EXAMPLE 10

*Rhodococcus sp.* MT 20118 (FERM BP-3934) was inoculated in 5000 ml of a liquid medium (pH 7.0) containing 1% of meat extract, 1% of peptone, 0.5 % of NaCl and 0.2 % of crotonamide, and cultivated therein by shaking culture at 28° C. for 50 hours. The cells were separated from the culture liquid by centrifugation, washed and then collected. 75 ml of 50 mM potassium phosphate buffer (pH 6.8), 8.4 g of acrylamide, 0.8 g of dimethylaminomethyl methacrylate and 0.8 g of methylenebisacrylamide were uniformly blended, and 100 g of the washed cells (corresponding to 27 g of dry cells) were suspended therein. To this were added 5 ml of 10 % dimethylaminopropionitrile and 10 ml of 5 % potassium persulfate and uniformly blended, which were polymerized and gelled in ice-water. The cells-containing gel was broken into small fragments in a blender and blended with 600 ml of 50 mM potassium phosphate buffer (pH 6.8) and 1 ml of 50 % glutaraldehyde. The mixture was treated in ice-water with gently stirring for 30 minutes. After washed, immobilized cells were obtained. Reaction was effected in such a way that 35 g of the immobilized cells were added to 50 ml of an aqueous solution containing 28 g/liter of acetone and 0.15 g per hour of acetone cyanohydrin was continuously added thereto with a pump with gently stirring at 6° C., whereupon the pH value of the reaction system was adjusted to be 8.5 with NaOH. After 40 hours, 101 g/liter of α-hydroxyisobutyramide was found to have accumulated in the reaction solution. The molar yield was 78 %.

ADVANTAGE OF THE INVENTION

In accordance with the present invention, α-hydroxyisobutyramide is efficiently produced by reacting a culture liquid of microorganisms having an ability of producing α-hydroxyisobutyramide from acetone cyanohydrin or the cultivated cells of the microorganisms or the processed cells of them, to acetone cyanohydrin in an aqueous medium.

In addition, α,β-unsaturated carboxylates of aliphatic alcohols or α,β-unsaturated carboxylic acids are produced by reacting the α-hydroxyisobutyramide and water and/or an aliphatic alcohol in the presence of a solid acid catalyst at a temperature of 150° C. or higher in a gaseous phase or in a gaseous-liquid mixed phase.

MICROORGANISMS DEPOSITED

*Rhodococcus erythropolis* MT-20082 (FERM BP-3933) and *Rhodococcus* sp. MT-20118 (FERM BP-3934) were deposited as Nos. FERM BP-3933 and FERM BP-3934, respectively, under the Budapest Treaty on Jul. 16, 1992 at Fermentation Research Institute, Agency of Industrial Science and Technology, Ministry of International Trade and Industry, of 1-3, Higashi 1 chome, Tsukuba-shi, Ibaraki-ken 305, Japan.

We claim

1. A method of producing α-hydroxyisobutyramide, which comprises the steps of:
   (a) culturing a microorganism effective for producing α-hydroxyisobutyramide from acetone cyanohydrin in a cultivation medium to produce cultured cells of the microorganism and a culture liquid, wherein said microorganism is selected from the group consisting of *Rhodococcus erythropolis* ATCC 4277, ATCC 11048 and FERM BP-3933;
   (b) reacting the culture liquid obtained from culturing said microorganism, the cultured cells of the microorganism, or the processed cells of the cultured microorganism, with acetone cyanohydrin in an aqueous reaction solution to form α-hydroxyisobutyramide in the aqueous reaction solution; and
   (c) thereafter recovering α-hydroxyisobutyramide from said aqueous reaction solution.

2. The method according to claim 1, wherein acetone is added to the aqueous reaction solution in step (b).

3. The method according to claim 2, wherein the amount of acetone to be added to the aqueous reaction solution is 4M or less.

4. A method of producing α-hydroxyisobutyramide, which comprises the steps of:
   (a) culturing a microorganism effective for producing α-hydroxyisobutyramide from acetone cyanohydrin in a cultivation medium to produce cultured cells of the microorganism and a culture liquid, wherein said microorganism is *Rhodococcus* sp. FERM BP-3934;
   (b) reacting the culture liquid obtained from culturing said microorganism, the cultured cells of the microorganism, or the processed cells of the cultured microorganism, with acetone cyanohydrin in an aqueous reaction solution to form α-hydroxyisobutyramide in the aqueous reaction solution; and
   (c) thereafter recovering α-hydroxyisobutyramide from said aqueous reaction solution.

5. The method according to claim 4, wherein acetone is added to the aqueous reaction solution in step (b).

6. The method according to claim 5, wherein the amount of acetone to be added to the aqueous reaction solution is 4M or less.

7. A method of producing α-hydroxyisobutyramide, which comprises the steps of:
   (a) culturing a microorganism effective for producing α-hydroxyisobutyramide from acetone cyanohydrin in a cultivation medium to produce cultured cells of the microorganism and a culture liquid, wherein said microorganism is *Arthrobacter paraffineus* ATCC 21003;
   (b) reacting the culture liquid obtained from culturing said microorganism, the cultured cells of the microorganism, or the processed cells of the cultured microorganism, with acetone cyanohydrin in an aqueous reaction solution to form α-hydroxyisobutyramide in the aqueous reaction solution; and
   (c) thereafter recovering α-hydroxyisobutyramide from said aqueous reaction solution.

8. The method according to claim 7, wherein acetone is added to the aqueous reaction solution in step (b).

9. The method according to claim 8, wherein the amount of acetone to be added to the aqueous reaction solution is 4M or less.

10. A method of producing α-hydroxyisobutyramide, which comprises the steps of:
    (a) culturing a microorganism effective for producing α-hydroxyisobutyramide from acetone cyanohydrin in a cultivation medium to produce cultured cells of the microorganism and a culture liquid, wherein said microorganism is *Achromobacter xerosis* IFO 12668;
    (b) reacting the culture liquid obtained from culturing said microorganism, the cultured cells of the microorganism, or the processed cells of the cultured microorganism, with acetone cyanohydrin in an aqueous reaction solution to form α-hydroxyisobutyramide in the aqueous reaction solution; and
    (c) thereafter recovering α-hydroxyisobutyramide from said aqueous reaction solution.

11. The method according to claim 10, wherein acetone is added to the aqueous reaction solution in step (b).

12. The method according to claim 11, wherein the amount of acetone to be added to the aqueous reaction solution is 4M or less.

13. A method of producing α-hydroxyisobutyramide, which comprises the steps of:

(a) culturing a microorganism effective for producing α-hydroxyisobutyramide from acetone cyanohydrin in a cultivation medium to produce cultured cells of the microorganism and a culture liquid, wherein said microorganism is *Acinetobacter calcoaceticus* IFO 12552;

(b) reacting the culture liquid obtained from culturing said microorganism, the cultured cells of the microorganism, or the processed cells of the cultured microorganism, with acetone cyanohydfin in an aqueous reaction solution to form α-hydroxyisobutyramide in the aqueous reaction solution; and (c) thereafter recovering α-hydroxyisobutyramide from said aqueous reaction solution.

14. The method according to claim 13, wherein acetone is added to the aqueous reaction solution in step (b).

15. The method according to claim 14, wherein the amount of acetone to be added to the aqueous reaction solution is 4M or less.

16. A method of producing α-hydroxyisobutyramide, which comprises the steps of:

(a) culturing a microorganism effective for producing α-hydroxyisobutyramide from acetone cyanohydrin in a cultivation medium to produce cultured cells of the microorganism and a culture liquid, wherein said microorganism is *Pseudomonas fluorescens* IFO 3925;

(b) reacting the culture liquid obtained from culturing said microorganism, the cultured cells of the microorganism, or the processed cells of the cultured microorganism, with acetone cyanohydrin in an aqueous reaction solution to form α-hydroxyisobutyramide in the aqueous reaction solution; and (c) thereafter recovering α-hydroxyisobutyramide from said aqueous reaction solution.

17. The method according to claim 16, wherein acetone is added to the aqueous reaction solution in step (b).

18. The method according to claim 17, wherein the amount of acetone to be added to the aqueous reaction solution is 4M or less.

* * * * *

UNITED STATES PATENT AND TRADEMARK OFFICE
CERTIFICATE OF CORRECTION

PATENT NO. : 5,443,973

DATED: : August 22, 1995

INVENTOR(S) : Ken-ichi ISHIWATA et al

It is certified that error appears in the above-identified patent and that said Letters Patent is hereby corrected as shown below:

On title page,

In the Title [54], delete "NITRIL" and insert therefor --NITRILE--.

Item
[75] Inventors: delete "Kenichi Sshiwata" and insert therefor --Ken-ichi Ishiwata--.

Item
[22] Filed: delete "19" and insert therefor --14--.

Item [56]
In Other Publications, line 3, delete "Enzymelic" and insert therefor --Enzymatic--; and line 6, delete "Solvent" and insert therefor --Solvents--.

IN THE CLAIMS:
Column 8,
Claim 13, line 10, delete "cyanohydfin" and insert therefor --cyanohydrin--.

Signed and Sealed this

Ninth Day of July, 1996

Attest:

BRUCE LEHMAN

*Attesting Officer*   *Commissioner of Patents and Trademarks*